(12) United States Patent
Van Loo et al.

(10) Patent No.: US 6,500,805 B2
(45) Date of Patent: Dec. 31, 2002

(54) FRUCTAN CONTAINING COMPOSITION FOR THE PREVENTION AND TREATMENT OF COLON CANCER AND METHOD FOR THE PREVENTION AND TREATMENT OF SAME

(75) Inventors: Jan Van Loo, Leuven (BE); Anne Frippiat, Sterrebeek (BE)

(73) Assignee: Tiense Suikerraffinaderij N.V. (BE)

( * ) Notice: Subject to any disclaimer, the term of this patent is extended or adjusted under 35 U.S.C. 154(b) by 0 days.

(21) Appl. No.: 09/424,168

(22) PCT Filed: May 14, 1998

(86) PCT No.: PCT/EP98/02864

§ 371 (c)(1),
(2), (4) Date: Nov. 19, 1999

(87) PCT Pub. No.: WO98/52578

PCT Pub. Date: Nov. 26, 1998

(65) Prior Publication Data

US 2002/0177561 A1 Nov. 28, 2002

(30) Foreign Application Priority Data

May 20, 1997 (EP) .............................. 97870069

(51) Int. Cl.$^7$ ........................ A61K 31/733; C08B 37/18
(52) U.S. Cl. ...................... 514/23; 514/54; 536/123.12; 426/658
(58) Field of Search ................ 514/23, 54; 536/123.12; 426/658

(56) References Cited

U.S. PATENT DOCUMENTS

| | | | | |
|---|---|---|---|---|
| 5,422,346 A | * | 6/1995 | Mitchell et al. | 514/54 |
| 5,563,173 A | * | 10/1996 | Yatsu et al. | 514/557 |
| 5,721,345 A | * | 2/1998 | Roberfroid et al. | 636/4.1 |
| 6,043,229 A | * | 3/2000 | Kettlitz et al. | 514/60 |

FOREIGN PATENT DOCUMENTS

| | | | |
|---|---|---|---|
| EP | 0692252 | 1/1996 | A61K/31/72 |
| JP | 60-089427 | 5/1985 | A61K/35/78 |
| JP | 63-093729 | 4/1988 | A61K/39/395 |
| JP | 02-172921 | 7/1990 | A61K/35/78 |

OTHER PUBLICATIONS

Van Loo, J. et al "Functional food properties of non–digestible oligosaccharides . . . " Br. J. Nutr. vol. 81 No. 2 pp. 121–132, 1999.*

Gallaher, D. et al "Probiotics, cecal microflora, and aberrant crypts in the rat colon" J. Nutr. vol. 126 pp. 1362–1371, 1996.*

Wang, X. et al. "Effects of the in vitro fermentation of oligofructose and inulin . . . " J. Appl. Bact. vol. 75 pp. 373–380, 1993.*

Scheppach, W. et al. "Role of short–chain fatty acids in the prevention of colorectal cancer" Eur. J. Cancer vol. 31A Nos. 7/8 pp. 1077–1080, 1995.*

CAS abstract of JP 57018982, 1982.*

Reddy, B. et al. "Inhibitory effect of *Bifidobacterium longum* on colon, mammary, and liver carcinogenesis . . . "Cancer res. vol. 53 pp. 3914–3918, 1993.*

Hambly et al., "Effects of High and low risk diets on biomarkers of colon cancer in human–flora–associated (HFA) rats" Anticancer Research, vol. 15, No. 5a, 1995, pp. 1656–1567.

Gibson et al., "Selective stimulation of bifidobacteria in the human colon by oligofructose and inulin" Gastroenterology, vol. 108, No. 4, 1995, pp. 975–982.

Reddy et al., "Effect of dietary oligofructose and inulin on colonic preneoplastic aberrant crypt foci inhibition" Carcinogenesis, vol. 18, No. 7, Jul. 1997, pp. 1371–1374.

Rowland et al., "Effect of bifidobacterium longum and inulin on gut bacterial metabolism and carcinogen–induced aberrant crypt foci in rats" Carcinogenesis, vol. 19, No. 2, Feb. 1998, pp. 281–285.

\* cited by examiner

*Primary Examiner*—James O. Wilson
*Assistant Examiner*—Leigh C. Maier
(74) *Attorney, Agent, or Firm*—Hayes Soloway P.C.

(57) ABSTRACT

The use is provided of a fructran with an average degree of polymerisation of at least 15 for the manufacture of a composition for the prevention and/or treatment of colon cancer in non-bovine mammals, particularly in human beings.

Also provided is a method of prevention and treatment of colon cancer in a non-bovine mammal, particularly in a human being, comprising administering to said mammal a composition comprising an effective dose of a fructan with an average degree of polymerisation of at least 15.

The said composition can be a medicament as well as a functional food. In a preferrred embodiment the fructan is inulin, more preferably inulin with an average degree of polymerisation of at least 20.

22 Claims, No Drawings

FRUCTAN CONTAINING COMPOSITION FOR THE PREVENTION AND TREATMENT OF COLON CANCER AND METHOD FOR THE PREVENTION AND TREATMENT OF SAME

FIELD OF THE INVENTION

The present invention relates to the use of certain fructans, preferably certain inulins, for the manufacture of a composition for the prevention and/or treatment of colon cancer in non-bovine mammals.

The present invention also relates to the use of compositions comprising certain fructans, preferably certain inulins, for the prevention and/or treatment of colon cancer in non-bovine mammals, and to a method of prevention and/or treatment of colon cancer in non-bovine mammals.

BACKGROUND OF THE INVENTION

Cancer in mammals is a disease which is already known from Ancient Times. Nowadays cancer, particularly lung, breast and colon cancer, has become one of the major causes of death of non-bovine mammals, in particular of humans, in the industrialised world.

The cancer disease is known to proceed in several steps, including genesis of cells of modified genome and functionality resulting in the formation of malignant cells; uncontrolled local proliferation of the malignant cells and invasion of adjacent normal body structures; and metastasis. During metastasis malignant cells are spread in a body cavity and/or throughout the body via the blood stream and/or the lymph, with invasion of various normal body structures. The invasion of the normal body structures results in their malfunctioning and/or destruction, eventually leading to the death of the affected mammal.

Various factors which can provoke carcinogenesis and cancer have already been identified, including certain viral infections, exposure to ionising radiation, exposure to certain mineral fibres, exposure to chemical mutagens, and improper diet.

As a result thereof various preventive measures have been introduced which have shown to be successful in preventing or reducing the occurrence of certain cancers.

Furthermore, various surgical and chemotherapeutical methods have been developed for the treatment of cancer. According to the type of cancer, the stage of the disease and the particulars of the affected mammal, these methods have been shown effective to a more or lesser degree.

Many reliable animal models for the study of the genesis and evolution of various cancers are available at present, enabling the evaluation of the preventive and curative properties of miscellaneous chemicals and dietary products.

Epidemiological studies in combination with studies on animal models have lead to the identification of dietary fibres as an important factor in the prevention and inhibition of certain cancers in mammals.

Dietary fibres are commonly defined as components of plant cells which are resistant to hydrolysis by the alimentary enzymes of man. Dietary fibres comprise cellulose, hemicellulose, polysaccharides, pectin, gums, waxes and lignin. According to this definition, fructans, which are soluble and edible polysaccharides, are dietary fibres. Fructans are composed of chains of carbohydrates which consist mostly of fructose units and in which fructosyl-fructose linkages constitute the majority of the linkages. Fructans commonly occur as polydisperse carbohydrates. They occur in plants, but they also can originate from bacterial activity and they can be synthesised enzymatically as well. All these fructans present typical dietary fibre properties; they are embraced by the present invention and are referred to herein as fructan(s).

Fructans are well known compounds including levan and inulin carbohydrates. Levans are D-fructans generally consisting of chains of fructose units which are essentially connected to each other by $\beta(2\text{-}6)$ linkages. Inulins are also D-fructans generally consisting of chains of fructose units but which are essentially connected to each other by $\beta(2\text{-}1)$ linkages. Most of the inulin chains terminate in one glucose unit.

Levans may occur as linear chain carbohydrates but they are mostly composed of branched fructose chains, whereas inulins are generally composed of linear chain carbohydrates but they may also occur as chains of fructose units which are branched to a larger or lesser extent. Levans and inulins which are suitable according to the present invention include linear and branched chain carbohydrates, as well as mixtures of said linear and branched chain carbohydrates.

Inulins occur in many plants and crops and can occur at concentrations of about 10 to 20% on fresh weight in chicory, dahlia tubers and Jerusalem artichoke. They can be isolated from these plants, purified, and optionally refined to remove impurities and undesired fractions of carbohydrates, at industrial scale, according to well known techniques.

Inulins can be represented by the general formulae $GF_n$ and $F_m$ wherein G represents a glucose unit, F represents a fructose unit, n represents the number of fructose units linked to the terminal glucose unit, and m represents the number of fructose units linked to each other in the carbohydrate chain. The number of saccharide units (fructose and glucose units) in one fructan molecule, i.e. the values n+1 and m in the above formulae, are commonly referred to as the degree of polymerisation and represented as (DP). Often the parameter average degree of polymerisation $(\overline{DP})$ is used too, which is the value corresponding to the total number of saccharide units divided by the total number of saccharide molecules present in a given (poly)saccharide composition.

Inulin from plant origin is a polydisperse composition of fructose chains with a degree of polymerisation (DP) ranging from 2 to about 100, whereas inulin from bacterial origin usually has a higher degree of polymerisation.

Fructans, including inulins of general formulae $GF_n$ and $F_m$, with a lower degree of polymerisation, usually defined as a (DP)<10, are commonly named oligofructoses and are referred to herein accordingly.

Inulin is commercially available. For example, inulin from chicory is available as RAFTILINE® from ORAFTI, (Tienen, Belgium), in various grades. Typical RAFTILINE® grades are, for example, ST, ST-Gel and GR (which have an average degree of polymerisation $(\overline{DP})$ of 10 and contain in total about 8% by weight glucose, fructose and sucrose), LS (which has also an average degree of polymerisation of 10 but which contains in total less than 1% by weight glucose, fructose and sucrose), and HP (high performance inulin) and HP-Gel (which have an average degree of polymerisation of $\geq 23$, commonly about 25, and are essentially free of glucose, fructose and sucrose).

Oligofructoses are usually obtained by partial, acidic or enzymatic hydrolysis of inulins and can also be obtained by enzymatic synthesis from sucrose, according to techniques which are well-known in the art. Oligofructoses are commercially available. Several grades of oligofructose are, for example, available from ORAFTI, (Tienen, Belgium), as RAFTILOSE®, e.g. RAFTILOSE® P95 which contains about 95% by weight oligofructoses with a degree of polymerisation ranging from 2 to 7 and about 5% by weight in total of glucose, fructose and sucrose.

STATE OF THE ART

Dietary fibres, in particular fructans, are known to have effects on various physiological functions and mechanisms in mammals.

In non-bovine mammals, these fibres are almost not metabolised in the mouth, the stomach and the small intestine, and they thus almost quantitatively enter the large intestine where they are completely fermented by the colonic microflora. This phenomenon results in various beneficial health effects in non-bovine mammals such as, for example, a reduction of the intestinal transit time, a decrease of the intestinal pH, a bifidus stimulating activity in the colon, an increase of the stool weight (bulking) and stool frequency.

Fructans, particularly inulin, are also known to have a beneficial effect on lipid metabolism , including a lowering effect on blood cholesterol and on serum triglycerides, and an increasing effect on the HDL/LDL ratio.

P. D. Cooper et al., Molecul. Immunol., 23 (8), 895, (1986), describe the activation of the alternative pathway of complement by gamma-inulin (a specific polymorphic form of dahlia inulin), and it is known that an activator of the alternative pathway of complement can have a potential non-specific anti-tumour effect.

Furthermore, fructans, particularly inulin, are described to have potential in the prevention and inhibition of cancer.

P. D. Cooper et al., (Molecul. Immunol., 23 (8), 903, (1986) have demonstrated that intraperitoneally injected gamma-inulin can prolong the survival of melanoma bearing mice.

It has also been disclosed that cultures of bifidobacteria inhibit 2-amino-3-methyl-imidazol[4,5-f]quinoline induced colon, liver, and mammary carcinogenesis (B. S. Reddy et al., Cancer Res., 53, 3914–3918, (1993) and azoxymethane-induced colon carcinogenesis (N. Kulkarni et al., Proc. Soc. Exptl. Biol. Med., 207, 278–283, (1994) in rats.

European patent application EP 0 692 252 A1 discloses the suppressing effect of the oligofructose RAFTILOSE® P95 (ex ORAFTI, Belgium; consisting of 95% of oligofructose chains with a degree of polymerisation (DP) between 2 and 7) and of the inulins RAFTILINE® ST, GR and LS, (defined hereinbefore and having an average degree of polymerisation of about 10) on breast carcinogenesis induced by injection of N-methylnitrosourea (MNU) in rats as well as on the growth of the transplantable TLT tumour (Taper Liver Tumour) in mice. The investigated oligofructose and inulins showed to have about equal carcinogenesis protective and cancer inhibiting effects.

Furthermore, the relation between the intake of dietary fibres and the reduction of the risk of colon cancer has been disclosed in several publications, e.g. J. Potter et al., Principles of Chemoprevention, IARC Scientific Publication N 139, 61–90, (1996); G. R. Howe et al., J. Natl. Cancer Inst., 84, 1887–1896, (1992); and B. S. Reddy et al., Gastoenterol., 102, 1475–1482, (1992).

However, in spite of the enormous efforts already made in the fight against cancer diseases, and colon cancer in particular, the prevention and successful inhibition and curing of colon cancer is not always possible yet. Therefore;

Medicine is still looking for improving the prevention, inhibition and curing of colon cancer. For various reasons such as the patient's comfort, chemotherapeutical methods are most preferred. Accordingly, there is a continuously ongoing search for improved and/or alternative compositions and therapeutical methods presenting a beneficial effect with respect to the inhibition and/or treatment of colon cancer, and/or presenting less undesirable side effects compared to known compositions and therapeutical methods.

DESCRIPTION OF THE INVENTION

The applicant is providing by the present invention a solution to one or more of the above mentioned problems, which even may present additional advantages.

By the term colon cancer is meant herein the colon cancer disease in any of its steps, including colon carcinogenesis, the formation of malignant cells in the colon, proliferation of said malignant cells and formation of tumours in the colon and/or invasion of normal colon structures by said malignant cells.

The invention is based on the findings made by the inventors during extensive studies that fructans with a higher degree of polymerisation, in particular fructans having an average degree of polymerisation of 15 or higher, present improved preventive and inhibiting properties against colon cancer in non-bovine mammals compared to fructans with a lower degree of polymerisation.

In view of the prior art, it could be expected that fructans with a higher degree of polymerisation, could, as do certain fructans with a lower degree of polymerisation, have preventive and/or inhibitive properties against colon cancer. However, the surprising findings of the inventors that fructans, in particular inulins, with a higher average degree of polymerisation, present significantly enhanced preventive and inhibiting properties against colon cancer in non-bovine mammals, compared to fructans with a lower average degree of polymerisation, could not be expected at all having regard to the state of the art.

Accordingly, in one aspect, the present invention relates to the use of a fructan with an average degree of polymerisation of at least 15 for the manufacture of a composition for the prevention and/or treatment of colon cancer in non-bovine mammals, particularly in human beings.

In another aspect, the invention relates to the use of a composition comprising a fructan with an average degree of polymerisation of at least 15, for the prevention and/or treatment of colon cancer in non-bovine mammals, particularly human beings.

In a further aspect, the invention relates to a method for the prevention and/or treatment of colon cancer in non-bovine mammals, particularly human beings, by administering to said mammal susceptible of colon cancer, in need of such prevention or treatment, a composition comprising an effective dose of a fructan with an average degree of polymerisation of at least 15.

In one preferred embodiment, the fructan is levan, preferably with an average degree of polymerisation of at least 20, more preferably ranging from 20 to 50.

In another preferred embodiment, the fructan is inulin, preferably with an average degree of polymerisation of at least 20, even more preferably ranging from 20 to 70. In a further preferred embodiment, the inulin has an average degree of polymerisation ranging from 20 to 40. A typically preferred inulin has an average degree of polymerisation about 25.

Inulin essentially consisting of linear polysaccharide chains or inulin containing up to about 2% by weight branched polysaccharide chains, are suitable according to the invention, but inulin containing a higher percentage of branched chains and even inulin essentially consisting of branched polysaccharide chains, and even mixtures of said linear and branched inulins, are suitable as well according to the invention. Typical inulins suitable according to the present invention are chicory inulins, for example RAFTILINE® HP and RAFTILINE® HP-Gel (both high performance inulins [in short HP inulin] ex ORAFTI, Belgium), with an average degree of polymerisation of about 25.

By the term composition according to the present invention is meant herein a medicament, (i.e. a composition which has a prophylactic and/or a curative effect on a mammal to which it has been administered), as well as a functional food, (i.e. a food product for human beings or for a non-human mammal, containing an additional functional ingredient, and which apart from its nutritional properties, additionally provides to that being one or more beneficial physiological effects). In the functional food compositions according to the present invention, said additional functional ingredient is meant to be a fructan, including levans and inulins, as defined herein before. Typical beneficial physiological effects are, for example, beneficial effects on the digestive tract, effects on lipid metabolism and preventive effects against cancer, in particular colon cancer.

When, in accordance with the present invention, the composition is a medicament, it can consist of the defined fructan or it can comprise said fructan in combination with any pharmaceutically acceptable carrier, and optionally also in combination with one or more physiologically active compounds, drugs or prodrugs. Said medicament can have any form known in the art, and can be administered according to known methods. Preferably, the medicament is in the form of a powder, a tablet, a soft gel capsule, a syrup, a solution or a suspension, and is administered orally. However, when present in an appropriate galenic form, the composition can also be administered parenterally, via tube feeding or rectally.

When the composition according to the present invention is a functional food, it is orally administered and it can be present in any known food form, such as, for example, a table spread, a dairy product such as e.g. a milk, a dairy dessert, a yoghurt, or a cheese, an alcoholic or non-alcoholic drink, a bakery product, a chocolate, an ice cream, a meat product, a fruit preparation, a confectionery product, a cereal product, a sauce, a soup, a snack, a dry mix, a meal replacer, a pet food, and the like.

The daily dosis effective in providing prevention against colon cancer preferably ranges, depending from the mammal species and the fructan species, from 0.01 to 2 g/kg body weight, more preferably from 0.05 to 0.5 g/kg body weight.

The daily dosis effective in providing an inhibitive and/or curing effect on colon cancer preferably ranges, depending from the mammal species, the fructan species and the stage of development of the colon cancer, from 0.2 to 3 g/kg body weight, more preferably from 0.5 to 1.5 g/kg body weight.

In the method of prevention and/or treatment, including inhibition and/or curing, of colon cancer in non-bovine mammals, preferably human beings, the daily dose of the composition according to the present invention described hereinbefore, can be administered to a said mammal susceptible of colon cancer and in need for such treatment, according to known methods in one or more unit doses during a shorter or longer period of time, in function of strength of the effect provided by the composition. When the composition is a functional food and a preventive effect is aimed at, the functional food is advantageously administered in one or more forms over a longer period of time, most preferably during the whole lifetime of the mammal.

Besides the improved physiological, prophylactic and/or therapeutical effects of the fructans with a higher degree of polymerisation compared to fructans with a lower degree of polymerisation, the compositions and method of treatment according to the present invention present significantly additional advantages. The compositions, for example, are easy to take in or to administer, and the method of treatment is easy to apply, without significant discomfort for the concerned mammal. Furthermore, the presence of fructan chains with a higher degree of polymerisation reduces certain discomforts often encountered with the intake of non-digestible carbohydrates such as e.g. soft stools, diarrhea, flatulence, bloating and intestinal cramps. A further considerable advantage presented by the fructans, in particular the preferred chicory inulin, relating to the present invention, is that they are naturally occurring, biodegradable products which are deprived of toxic effects and that they can be taken in and administered to newborn as well as adult, including pregnant, and aged mammals. Compared to many known chemotherapeutical compositions, the intake of, administration of, and the treatment with a composition comprising the above defined fructans according to the present invention, is usually very well supported by the mammal and does not provoke significant undesirable side effects or a significant discomfort, if any at all, to the mammal. Furthermore, the fructans suitable according to the present invention are largely commercially available at acceptable cost.

EXPERIMENTAL PART

In support of the present invention, the following illustrative experimental data are given regarding a study made to determine the effect of oligofructose and HP inulin on carcinogen-induced colonic aberrant crypt foci (ACF) formation in rat.

Aberrant crypt foci (ACF), which are recognized as early preneoplastic lesions in the colon, have consistently been observed in experimentally induced colon carcinogenesis in laboratory animals (McLellan, E. A. et al., *Cancer Res.*, 51, 5270–5274, (1991) and Wargovich, M. H., et al., *Cancer Epidemiol Biomarkers & Prev.*, 5, 355–360, (1996)). Pretlow, T. P., et al., *J. Cell. Biochem.*, 16G (Suppl.), 55–62, (1992), have also shown that these lesions are present in the colonic mucosa of patients with colon cancer and have suggested that aberrant crypts are putative precursor lesions from which adenomas and carcinomas may develop in the colon. ACF express mutations in the apc gene and ras oncogene that appear to be biomarkers of colon cancer development (Vivona, A. A., et al., *Carcinogenesis* (Lond.) 14, 1777–1781, (1993)). There is some evidence that several inhibitors of ACF formation reduce the incidence of colon tumors in laboratory animals (Wargovich, M. H., et al., *Cancer Epidemiol Biomarkers & Prev.*, 5, 355–360, (1996) ), suggesting that ACF induction can be used to evaluate novel agents for their potential chemopreventive properties against colon cancer.

MATERIALS AND METHODS

Animals, Diets, Carcinogen, and Chemopreventive Agents

Azoxymethane (AOM) was obtained from Ash Stevens (Detroit, Mich., USA). RAFTILOSE® P95 and RAFTILINE® HP which contained on dry matter mainly oligofructose (95%) and inulin (99.5%), respectively, were obtained from ORAFTI (Tienen, Belgium). RAFTILOSE® which was produced by partial enzymatic hydrolysis of chicory inulin is a polydisperse β [2-1] fructan with a (DP) ranging between 2 and 7 and a (DP) of 4.5. RAFTILINE® HP (i.e. high performance inulin and abbreviated herein to HP inulin) is chicory inulin of which the lower (DP) fraction has been removed. Its (DP) ranges between 10 and 60 and it has a $\overline{(DP)}$ of 25. This choice of test substrates thus allows to observe effects of the degree of polymerisation.

Weanling male F344 rats were obtained from Charles River Breeding Laboratories (Kingston, N.Y., USA). All ingredients of the AIN-76A semipurified diet were obtained from Dyets Inc., (Bethlehem, Pa., USA) and were stored at 4° C. until the experimental diets were prepared. The percentage composition of semipurified diet is as follows: casein, 20; D,L-methionine, 0.3; corn starch, 52; dextrose, 13; corn oil, 5; alphacel, 5; mineral mix (AIN-76A), 3.5; vitamin mix (AIN-76A), 1; and choline bitartrate, 0.2 (Reddy B. S., et al., Cancer Res., 48, 6642–6647, (1988). The rats were held in quarantine for 1 week and had access to modified AIN-76A semipurified control diet. They were randomly distributed by weight into various dietary groups and were transferred to an animal holding room where they were housed in plastic cages, three rats/cage, under controlled conditions of a 12 h light/12 h dark cycle, 50% relative humidity, and 21° C. room temperature. RAFTILOSE(®) and RAFTILINE® were added to the control diet at 10% level at the expense of starch.

Experimental procedure. Beginning at 5 weeks of age, groups of animals were fed the control or experimental diets. All animals except the vehicle-treated rats received AOM s.c. once weekly at 7 and 8 weeks of age at a dose rate of 15 mg/kg body weight/week. Animals intended for vehicle treatment were given an equal volume of normal saline. The rats were continued on control or experimental diets until the termination of the study, when they were 16 weeks of age. All animals were sacrificed by $CO_2$ euthanasia. The colons were removed, flushed with Krebs-Ringer solution, opened from cecum to anus, and fixed flat between two pieces of filter paper in 10% buffered formalin. After a minimum of 24 h in buffered formalin, the colons were cut into 2-cm segments, placed in a Petri dish containing 0.2% methylene blue in Krebs-Ringer solution and kept for 5–10 min. They were then placed, mucosal side up, on a microscope slide and observed through a light microscope. ACF were recorded according to standard procedures (McLellan E. A., et al., Cancer Res., 51, 5270–5274, (1991). Aberrant crypts were distinguished from the surrounding normal crypts by their increased size, significantly increased distance from lamina to basal surface of cells, and the easily discernible pericryptal zone. Crypt multiplicity was determined as the number of crypts in each focus and categorised as those containing up to three, or four or more aberrant crypts/focus. All colons were scored by one observer without knowing the identity of agents under study; scores were checked at random by a second observer.

Statistical Analysis. All results were expressed as the means ± SD and were analysed by one-tailed Student's t-test. Differences were considered statistically significant at $p<0.05$.

RESULTS

General Observations. The body weights of AOM-and vehicle-treated animals fed the control and experimental diets containing 10% inulin or oligofructose were comparable throughout the study (Table 1, hereafter). There were no signs of any adverse effects in liver, kidney, stomach, intestine or lungs of animals fed inulin or oligofructose.

Aberrant Crypt Foci. Table 2 hereafter summarises the AOM-induced ACF in the colon of rats fed the control and experimental diets. The animals administered saline (vehicle) and fed the control and experimentals diets containing inulin or oligofructose showed no evidence of ACF formation in the colon (data not shown). In the animals fed the control diet, AOM treatment induced on the average about 120 ACF/colon. ACF were predominantly observed in the distal colons. Efficacy end points used in this study were inhibition of the total number of ACF/colon as well as the reduction of the number of multicrypt clusters (2 or more) of aberrant crypts/focus. Administration of oligofructose or HP inulin in the diet significantly suppressed the total number of ACF/colon as compared to the control diet; the degree of inhibition was significantly more pronounced in the animals fed HP inulin ($p<0.006$) than in those fed oligofructose ($p<0.02$). Crypt multiplicity in terms of 2 or 3 aberrant crypts/focus was also significantly inhibited in animals fed HP inulin ($p<0.02-0.0001$) or oligofructose ($p<0.04-0.01$). Because multiplicity of aberrant crypts has been a probable predictor of colon tumor outcome (Pretlow, T. P., et al., Carcinogenesis (Lond.), 13. 1509–1512, (1992) ), the present study used this criterion to evaluate oligofructose and HP inulin for their potential inhibitory properties.

The results of the present study indicate that orally taken oligofructose and HP inulin inhibits AOM-induced colonic ACF formation in rats supporting the potential colon tumor inhibitory properties of chicory fructans. The experimental results clearly demonstrate that the preventive and ACF inhibitory properties provided by a fructan (in casu HP inulin ) with a higher average degree of polymerisation, are considerably enhanced compared to a fructan (oligofructose) with a lower average degree of polymerisation.

TABLE 1.

Body weights of animals fed the control diet and experimental diets containing oligofructose and HP inulin.

| Experimental groups | Body weights (grams) on control and experimental diets at week | | | |
|---|---|---|---|---|
| | 0 | 3 | 6 | 10 |
| AOM-treated | | | | |
| 1. Control diet | 119 ± 5.9[a] | 173 ± 9.1 | 257 ± 11 | 320 ± 14 |
| 2. Oligofructose, 10% | 119 ± 6.6 | 167 ± 9.8 | 258 ± 15 | 327 ± 16 |
| 3. HP Inulun, 10% | 120 ± 7.1 | 73 ± 7.8 | 259 ± 12 | 328 ± 15 |
| Saline-treated | | | | |
| 4. Control diet | 117 ± 8.5 | 179 ± 9.7 | 256 ± 9.8 | 329 ± 12 |
| 5. Oligofructose, 10% | 120 ± 5.9 | 175 ± 7.3 | 264 ± 9.3 | 338 ± 12 |
| 6. HP Inulin, 10% | 119 ± 5.7 | 171 ± 6.0 | 256 ± 8.1 | 329 ± 13 |

[a]Mean + SD

TABLE 2.

Effect of dietary oligofructose and HP inulin on colonic ACF formation in male F344 rats.

| Experimental groups | Total ACF/colon | Foci containing number of aberrant crypts | | | |
|---|---|---|---|---|---|
| | | 1 crypt/focus | 2 crypts/focus | 3 crypts/focus | 4 or more crypts/focus |
| Control diet | 120 ± 28 | 19.5 ± 7.3 | 43.7 ± 7.8 | 28.2 ± 7.5 | 28.3 ± 8.2 |
| Oligofructose, 10% | 92 ± 28[b] ($p < 0.024$) | 15.4 ± 7.5 | 31.2 ± 13[b] | 21.3 ± 7.8[b] ($p < 0.01$) | 23.9 ± 8.2 ($p < 0.04$) |
| HP Inulun, 10% | 78 ± 37[b] ($p < 0.006$) | 15.7 ± 8.2 | 24 ± 12[b] ($p < 0.0001$) | 16.6 ± 7.2[b] ($p < 0.02$) | 21.8 ± 14.2 |

[a]Mean ± SD
[b]Significantly different from the control diet. The level of significance is shown in parenthesis.

What is claimed is:

1. A method for inhibiting cancel in the colon of a non-bovine mammal susceptible to colon cancer, comprising the step of:
   administering to said mammal a composition comprising an effective dose of a fructan with an average degree of polymerisation of at least about 20.

2. Method according to claim 1 wherein said effective dose of said fructan is administered in one or more unit doses, a daily total of the one or more unit doses ranging from 0.01 to 2 g/kg body weight of said mammal.

3. Method according to claim 1 wherein the mammal is selected from the group consisting of a human being, a dog and a cat.

4. Method according to claim 3, wherein the fructan is a levan.

5. Method according to claim 3 wherein the fructan is an inulin.

6. Method according to claim 5 wherein the inulin has an average degree of polymerisation ranging from 20 to 40.

7. Method according to claim 1 wherein the composition is a functional food.

8. Method according to claim 1 wherein the composition is a medicament.

9. Method of treating colon cancer in a non-bovine mammal susceptible to colon cancer comprising the step of:
   administering to said mammal a composition comprising an effective dose of a fructan with an average degree of polymerisation of at least about 20.

10. Method according to claim 9 wherein said effective dose of said fructan is administered in one or more unit doses, a daily total of the one or more unit doses ranging from 0.01 to 2 g/kg body weight of said mammal.

11. Method according to claim 9 wherein the mammal is selected from the group consisting of a human being, a dog and a cat.

12. Method according to claim 9 wherein the composition is a functional food.

13. Method according to claim 9 wherein the composition is a medicament.

14. A method for inhibiting cancers in the colon of a non-bovine mammal susceptible to colon cancer, comprising the step of:
   obtaining a composition comprising a fructan with an average degree of polymerisation of at least about 20, and
   administering an effective dose of said composition to said non-bovine mammal.

15. The method of claim 14 wherein said non-bovine mammal is selected from the group consisting of a human being, a dog and a cat.

16. The method of claim 14, wherein the fructan is a levan.

17. The method of claim 14, wherein the fructan is an inulin.

18. The method of claim 17, wherein the inulin is chicory inulin with an average degree of polymerisation of about 25 and which is essentially free of glucose, fructose and sucrose.

19. The method of claim 14, wherein the composition is a medicament.

20. The method of claim 19, wherein the medicament comprises said fructan in combination with a pharmaceutically acceptable carrier.

21. The method of claim 20, wherein the medicament further comprises a selected one of a physiologically active compound, a drug, and a pro drug.

22. The method of claim 14, wherein the composition is a functional food.

* * * * *

UNITED STATES PATENT AND TRADEMARK OFFICE
CERTIFICATE OF CORRECTION

PATENT NO. : 6,500,805 B2 Page 1 of 1
DATED : December 31, 2002
INVENTOR(S) : Van Loo et al.

It is certified that error appears in the above-identified patent and that said Letters Patent is hereby corrected as shown below:

<u>Column 9,</u>
Line 16, "cancel" should be -- cancers --.

Signed and Sealed this

Twenty-eighth Day of October, 2003

JAMES E. ROGAN
*Director of the United States Patent and Trademark Office*